United States Patent [19]

Behre et al.

[11] Patent Number: 5,847,234
[45] Date of Patent: Dec. 8, 1998

[54] PROCESS FOR THE PREPARATION OF 4-HYDROXYBIPHENYL

[75] Inventors: Horst Behre, Odenthal; Helmut Fiege; Günter Rauchschwalbe, both of Leverkusen, all of Germany

[73] Assignee: Bayer Aktiengesellschaft, Leverkusen, Germany

[21] Appl. No.: 873,532

[22] Filed: Jun. 12, 1997

[30] Foreign Application Priority Data

Jun. 18, 1996 [DE] Germany .................. 196 24 202.9

[51] Int. Cl.$^6$ ...................................... C07C 39/12
[52] U.S. Cl. ........................................ 568/747; 568/748
[58] Field of Search .................... 568/731, 734, 568/743, 744, 778, 795, 807, 747, 748

[56] References Cited

U.S. PATENT DOCUMENTS 2,368,361  1/1945  Jenkins .
4,243,822  1/1981  Demier et al. .
4,467,123  8/1984  Mayer et al. .

FOREIGN PATENT DOCUMENTS 3031094  3/1981  Germany .
 358720  7/1960  Japan .
0116732  1/1989  Japan .
2071090  9/1981  United Kingdom .

Primary Examiner—Michael L. Shippen
Attorney, Agent, or Firm—Sprung Kramer Schaefer & Briscoe

[57] ABSTRACT

4-Hydroxybiphenyl is obtained in non-thixotropic form if a reaction mixture which is obtained by alkaline hydrolysis of biphenyl-4-sulfonic acid and contains 4-hydroxybiphenyl is heated at elevated pressure at above 115° C. and at a pH from 0 to below 6.5.

11 Claims, No Drawings

5,847,234

PROCESS FOR THE PREPARATION OF 4-HYDROXYBIPHENYL

BACKGROUND OF THE INVENTION

The present invention relates to a process for the preparation of 4-hydroxybiphenyl from biphenyl-4-sulfonic acid by alkaline hydrolysis and subsequent heating under pressure.

4-Hydroxybiphenyl is an important precursor for the preparation of plant protection agents and emulsifiers.

The patent literature discloses preparing 4-hydroxybiphenyl from biphenyl-4-sulfonic acid using an alkali melt, the sulfo group being replaced by the hydroxyl group. To the alkali melt is frequently added the sodium salt of said sulfonic acid which is obtained after the sulfonation of biphenyl with sulfuric acid, dilution of the sulfonation mixture with water, partial neutralization with sodium hydroxide solution, subsequent filtration and drying. Numerous patent publications describe an unpressurized alkali melt at occasionally very high temperatures (at least 380° C.) and long reaction times with relatively poor yields and product qualities. Attempts are made to decrease the high temperatures and viscosities of the melts by partially replacing NaOH by the much more expensive KOH and by using additives of various types. (JP 71-30507; German Offenlegungsschrift 3 031 094; GB 2 071 090; U.S. Pat. No. 2,368,361; JP 60-8720; JP 71-30508; JP 71-30509; JP 77-68154; JP 74-16417; JP 81-57728). All of the processes described are thus unsatisfactory with respect to the purity and yield of the product obtained or with respect to the high temperatures to be employed or the laboriousness of the process, for example when additives which have to separated off later are used.

U.S. Pat. No. 4,467,123 describes a process for preparing 4-hydroxybiphenyl from biphenyl-4-sulfonic acid by alkaline pressure hydrolysis at a temperature between 280° and 330° C. and at elevated pressure of up to 120 bar with 3 to 25 mol of aqueous alkali metal hydroxide per equivalent sulfonate group at a concentration of at least 50% by weight. However, replication of Example 2 of U.S. Pat. No. 4,467,123 for the preparation of 4-hydroxybiphenyl has shown that, although this product is produced in high purity with respect to the organic byproducts, it is produced in the form of a thixotropic moist product having a very high water content of 65–70% by weight, which virtually cannot be handled (see comparison example).

SUMMARY OF THE INVENTION

A process has now been found for the preparation of 4-hydroxybiphenyl in the form a non-thixotropic moist product from biphenyl-4-sulfonic acid by alkaline hydrolysis with alkali metal hydroxide, which comprises heating the alkaline reaction mixture, after dilution with water and neutralization with a mineral acid, at elevated pressure at a temperature >115° C. and a pH of 0 to <6.5.

DETAILED DESCRIPTION OF THE INVENTION

In the process according to the invention, the 4-hydroxybiphenyl can be prepared in any desired manner by alkaline hydrolysis of biphenyl-4-sulfonic acid with alkali metal hydroxide, for example by an unpressurized caking melt (powder melt), if appropriate also in the presence of a very high-boiling inert organic medium, or by an alkaline pressurized hydrolysis.

Preferably, the 4-hydroxybiphenyl is prepared by the process according to the invention by an alkaline pressurized hydrolysis at a temperature of 290°–340° C., in particular at 310° to 330° C., and at a pressure of up to 120 bar, for example 2 to 120 bar, preferably at 5 to 80 bar, particularly preferably at 10 to 40 bar. These pressures can be the inherent pressure of the reaction mixture or can be increased additionally to the inherent pressure by forcing in inert gas, for example nitrogen. The inherent pressure of the reaction mixture is a factor of the mixing and concentration ratios in the reaction mixture and of the established reaction temperature in a manner familiar in principle to those skilled in the art. This relationship applies particularly to the proportion of water in the reaction mixture. In the event that a pressure in the lower part of said ranges is to be established, this can therefore be achieved by letting off steam from the reaction mixture via a pressurizing valve. Aqueous alkali metal hydroxides for the process according to the invention which may be mentioned are, for example, aqueous solutions of sodium hydroxide or potassium hydroxide, preferably sodium hydroxide, having a concentration of at least 50% by weight of alkali metal hydroxide, based on the total weight of the aqueous solution. For example, a concentration of 50 to 96% by weight, preferably 60 to 95% by weight, particularly preferably 65 to 85% by weight, may be mentioned. The amount of the aqueous alkali metal hydroxide is such in this case that 3 to 25 mol of alkali metal hydroxide per 1 mol of alkali metal biphenylsulfonate, preferably 5 to 12 mol of alkali metal hydroxide per 1 mol of alkali metal biphenylsulfonate, are present in the reaction mixture. Said molar amounts of alkali metal hydroxide are based in this case on the sulfonate group which is, for example, the sodium salt or potassium salt of biphenyl-4-sulfonic acid.

Biphenyl-4-sulfonic acid is prepared in a known manner by sulfonation of biphenyl with sulfuric acid. The sulfonic acids obtainable in this case are then neutralized in a known manner to give the corresponding sulfonates. This neutralization can proceed outside the reaction mixture for the process according to the invention, so that a previously neutralized sulfonate is used in the process according to the invention. However, the neutralization to give the sulfonate can also proceed in the process according to the invention, so that the free biphenyl-4-sulfonic acid is used in the process according to the invention. According to the invention it is additionally possible to use the biphenyl-4-sulfonic acid or its alkali metal salts in dry or water-moist form or in the form of its aqueous solution. According to the invention, either the pure biphenyl-4-sulfonic acid or sulfonation mixtures can be used which contain biphenyl-4-sulfonic acid in addition to unreacted sulfuric acid and in addition to other biphenyl mono- and disulfonic acids. Preferably, for the process according to the invention, the biphenyl-4-sulfonic acid is used in the form of the water-moist sodium salt. Since, to prepare the 4-hydroxybiphenyl, the molar amount of aqueous alkali metal hydroxide is based on the sulfonate group, when the free biphenyl-4-sulfonic acid is used, or when sulfonation mixtures containing biphenyl-4-sulfonic acid are used, an additional amount of alkali metal hydroxide must be added which is sufficient for the complete neutralization of all acid groups.

In the process according to the invention, the alkaline reaction mixture is diluted with water and neutralized or slightly acidified with a mineral acid to a pH of 0 to <6.5, preferably 3 to <6.5, in particular 5 to <6.5, in order to release the 4-hydroxybiphenyl from the alkali metal salt initially formed in the alkali melt. Mineral acids which can be used in the process according to the invention are, for example, hydrochloric acid and/or sulfuric acid. Preferably, sulfuric acid is used, for example at a content of 10 to 100% by weight. The amount of water necessary for diluting the alkaline reaction mixture is chosen in the process according to the invention such that the alkali metal salts formed in the neutralization/acidification, for example sodium sulfate and/or sodium chloride, remain dissolved or are dissolved in the isolation of the 4-hydroxybiphenyl prepared by the process according to the invention.

It is essential for the isolation of 4-hydroxybiphenyl in the form of a non-thixotropic moist product by the process according to the invention that the neutralized/acidified reaction mixture is heated at elevated pressure at a temperature >115° C. and a pH of <6.5. Preferably, this heating is performed at temperatures of 120° to 170° C., particularly preferably at 125° to 155° C., in particular 130° to 145° C.

The heating time is dependent on the temperature selected and is generally 5 min to 5 h and, in the particularly preferred temperature range of 130° to 145° C., is approximately 15 min to 3 h.

The process according to the invention is carried out in the preferred embodiment in detail as below:

Sodium biphenyl-4-sulfonate is reacted with about 70% strength by weight NaOH to give sodium 4-phenylphenolate (about 320° C.; 16–26 bar), with the molar ratio of NaOH to biphenyl-4-sulfonate having to be about 10:1. The reaction mixture is diluted to a content of about 12% by weight of 4-hydroxybiphenyl by direct expansion at 320° C. to a water reservoir or by pumping water into the reaction mixture after prior cooling to 200° C. The resulting alkaline 4-hydroxybiphenyl sodium salt suspension is metered into a water reservoir simultaneously with roughly 50% strength by weight $H_2SO_4$ at 90° C. and a pH of 5.5. The resulting aqueous $Na_2SO_3$/$NaHSO_3$-containing 4-hydroxybiphenyl suspension having a content of about 4.3% by weight of 4-hydroxybiphenyl is then heated at 130°–135° C. and about 2 bar for about 2 h, stirred cold at 10 K/h to 100° C. and then further to 60° C. The highly readily filtering coarsely crystalline product is isolated at 60° C. via a glass sinter vacuum filter and washed with water. A virtually colorless flowable non-thixotropic substantially $Na_2SO_4$-free product having a drastically decreased water content of 10–20% by weight is obtained, in comparison with the highly thixotropic product containing 65–70% by weight of $H_2O$ obtained without the heating according to the invention.

The process according to the invention can be carried out batchwise and continuously.

EXAMPLE 1

A 5 l nickel autoclave was charged successively with 2000 g of NaOH (70%) and 953 g of sodium biphenyl-4-sulfonate (87.2% by weight of free acid, molecular weight 234). After flushing with nitrogen, the reaction mixture (suspension) was heated to 320° C. in the course of approximately 2 h, with the stirrer only being turned on once 180° C. has been reached, and the mixture was further stirred for approximately 7 h at 320° C. and a pressure of 16–26 bar. To dilute the reaction mixture, after cold stirring to 200° C. (approximately 2 h), 2000 g of water were pumped in and the autoclave, after further cooling to approximately 75° C., was completely drained. The resulting alkaline 4-hydroxybiphenyl sodium salt suspension having a content of approximately 12% by weight of 4-hydroxybiphenyl (by HPLC), molecular weight 170, was, simultaneously with 3370 g of $H_2SO_4$ (50%) at 90° C. and a pH of 5.5, metered into a reservoir of 5000 g of water in the course of approximately 1 h, approximately 13,320 g of aqueous $Na_2SO_3$/$NaHSO_3$-containing 4-hydroxybiphenyl suspension having a content of approximately 4.3% by weight of 4-hydroxybiphenyl (by HPLC) being obtained. 900 g of this aqueous 4-hydroxybiphenyl suspension were introduced into a 1.6 l glass autoclave. The reaction mixture was heated to 130°–135° C. with vigorous stirring (750 rpm) in the course of approximately ½ h, a pressure of approximately 2 bar being established and slight sintering of 4-hydroxybiphenyl being observed, heated at 130°–135° C. for 2 h, cold-stirred at 10 K/h to 100° C. and then further to 60° C. The very readily filtering, coarsely crystalline product was isolated at 60° C. via a glass sinter suction filter and washed with a total of 100 g of water in two equal portions. 46 g of 4-hydroxybiphenyl, moist (virtually colorless, flowable, non-thixotropic product), were obtained.

The isolated product had the following content as determined by HPLC:

83.0% by weight of 4-hydroxybiphenyl, molecular weight 170

17.0% by weight of water

<0.2% by weight of sulfate, molecular weight 96.

The yield of 4-hydroxybiphenyl was 94% of the theoretical yield, based on biphenyl-4 4-sulfonic acid used.

EXAMPLE 2 (For Comparison)

An amount of 900 g of an aqueous $Na_2SO_3$/$NaHSO_3$-containing 4-hydroxybiphenyl suspension, prepared as in Example 1, having a content of approximately 4.3% by weight of 4-hydroxybiphenyl (by HPLC) was cold-stirred from 90° C. to 60° C. The readily filtering product was isolated at 60° C. via a glass sinter suction filter and washed with a total of 300 g of water in two equal portions. 127 g of 4-hydroxybiphenyl, moist (virtually colorless, highly thixotropic product), were obtained.

The isolated product had the following content determined by HPLC:

31.0% by weight of 4-hydroxybiphenyl, molecular weight 170

69.0% by weight of water

<0.2% by weight of sulfate, molecular weight 96

The yield of 4-hydroxybiphenyl was 94% of the theoretical yield, based on biphenyl-4 4-sulfonic acid used. The handling and further processing of the highly thixotropic product were extremely problematical (eg. storage, charging and emptying of packages, difficult transfer to a suitable drying unit, uneconomically high drying costs because of the high $H_2O$ content).

What is claimed is:

1. A process for the preparation of 4-hydroxybiphenyl in the form of a non-thixotropic moist product with a water content of 10 to 20% by weight from biphenyl-4-sulfonic acid by alkaline hydrolysis with alkali metal hydroxide, which comprises heating the hydrolysis mixture, after dilution with water and neutralization with a mineral acid, at a temperature above 115° C. to 170° C. and at a pH of 0 to below 6.5.

2. The process of claim 1, wherein the neutralized hydrolysis mixture is heated at elevated pressure at a pH of <6.5 at temperatures of 120° to 170° C.

3. The process of claim 2, wherein the neutralized hydrolysis mixture is heated at 125° to 155° C.

4. The process of claim 3, wherein the neutralized hydrolysis mixture is heated at 130° to 145° C.

5. The process of claim 1, wherein the 4-hydroxybiphenyl is obtained by an alkaline pressurized hydrolysis from biphenyl-4-sulfonic acid at a temperature of 290°–340° C., at a pressure of 2 to 120 bar, and at an alkali metal hydroxide concentration of 50 to 96% by weight, with the amount of the aqueous alkali metal hydroxide being such that 4 to 26 mol of alkali metal hydroxide are present in the hydrolysis mixture per 1 mol of biphenyl-4-sulfonic acid.

6. The process of claim 5, wherein the 4-hydroxybiphenyl is obtained by an alkaline pressurized hydrolysis from biphenyl-4-sulfonic acid at a temperature of 310° to 330° C.

7. The process of claim 5, wherein the 4-hydroxybiphenyl is obtained by an alkaline pressurized hydrolysis from biphenyl-4-sulfonic acid at a pressure of 5 to 80 bar.

8. The process of claim 7, wherein the 4-hydroxybiphenyl is obtained by an alkaline pressurized hydrolysis from biphenyl-4-sulfonic acid at a pressure of 10 to 40 bar.

9. The process of claim 5, wherein the 4-hydroxybiphenyl is obtained by an alkaline pressurized hydrolysis from biphenyl-4-sulfonic acid at an alkali metal hydroxide concentration of 60 to 95% by weight.

10. The process of claim 9, wherein the 4-hydroxybiphenyl is obtained by an alkaline pressurized hydrolysis from biphenyl-4-sulfonic acid at an alkali metal hydroxide concentration of 65 to 85% by weight.

11. The process of claim 5, wherein the amount of the aqueous alkali metal hydroxide is such that 5 to 12 mol of alkali metal hydroxide are present per 1 mol of alkali metal biphenylsulfonate.

* * * * *